United States Patent [19]

McCann

[11] Patent Number: 4,861,802

[45] Date of Patent: Aug. 29, 1989

[54] PREPARATION OF LOW MOLECULAR WEIGHT OLEFINIC HYDROCARBONS USING A PEROVSKITE CATALYST

[75] Inventor: Elrey L. McCann, Mendenhall, Pa.

[73] Assignee: E. I. Du Pont de Nemours and Company, Wilmington, Del.

[21] Appl. No.: 156,907

[22] Filed: Feb. 17, 1988

[51] Int. Cl.$^4$ ................................................ C07C 1/04
[52] U.S. Cl. .................................... 518/717; 518/716; 518/721; 518/713; 502/525
[58] Field of Search ................ 518/716, 717, 721, 713

[56] References Cited

U.S. PATENT DOCUMENTS 3,972,837  8/1976  Acres et al.
4,126,580  11/1978  Lauder
4,151,123  4/1979  McCann
4,171,320  10/1979  Vannice et al.
4,199,522  4/1980  Murchison
4,312,955  1/1982  Bartley ................................ 518/716

Primary Examiner—Howard T. Mars

[57] ABSTRACT

Improved process for the catalytic gas phase preparation of low molecular weight ($C_{2-6}$) olefinic hydrocarbons from mixtures of $H_2$ and CO, the improvement consisting of contacting and reacting a mixture of $H_2$ and CO, at a $H_2$/CO molar ratio within the range 0.3 to 1.5, at a space velocity of 1 to 100 minutes$^{-1}$, at a pressure of 1 to 2000 psia (6.894 kPa to 13.788 MPa), at a temperature within the range 200° to 400° C., in the presence of the catalyst of the empirical formula $AB_{1-a}Fe_aO_3$, wherein A, B and a are defined herein, for example, $LaFeO_3$.

11 Claims, No Drawings

PREPARATION OF LOW MOLECULAR WEIGHT OLEFINIC HYDROCARBONS USING A PEROVSKITE CATALYST

BACKGROUND OF THE INVENTION

1. Field of the Invention

This invention relates to the preparation of low molecular weight olefinic hydrocarbons from mixtures of carbon monoxide and hydrogen using a heterogeneous perovskite catalyst in a modified Fisher-Tropsch process.

2. Background

Commonly assigned U.S. Pat. No. 4,151,123 discloses catalysts which are useful for the oxidation of hydrocarbons and carbon monoxide and for the reduction of nitric oxide. The catalysts comprise an oxide of a transition metal having an atomic number of 23 to 30, 42 to 57 or 74 to 79 deposited on a second metal oxide having a perovskite structure.

U.S. Pat. No. 4,171,320 discloses catalysts which are useful for the preparation of hydrocarbons, with reduced methane formation, and for the selective production of olefinic hydrocarbons, preferably $C_{2-5}$ olefins. The feed comprises a carbon monoxide/hydrogen synthesis gas stream and the catalyst comprises ruthenium on a support comprising at least one refractory Group V-B metal oxide, preferably $V_2O_3$, $Nb_2O_5$ or $Ta_2O_5$.

U.S. Pat. No. 4,199,522 discloses an improved Fischer-Tropsch process for the preparation of olefinic hydrocarbons having two to four carbon atoms. The improvement comprises using a catalyst having a surface area less than about 100 m$^2$/g and consisting essentially of:

(1) at least one material selected from the group consisting of the sulfide, oxide or metal of Mo, W, Re, Ru, Ni, Pd, Rh, Os, Ir and Pt;

(2) at least one material selected from the group consisting of the hydroxide, oxide or salt of Li, Na, K, Rb, Cs, Mg, Ca, Sr, Ba and Th; and (3) optionally, a support.

It is an object of this invention to provide a modified Fischer-Tropsch process for the production of low molecular weight olefinic hydrocarbons from carbon monoxide/hydrogen synthesis gas. Another object is to provide a perovskite catalyst which is useful in such a process. Still another object is to provide such a catalyst, for use in such a process, to produce low molecular weight olefinic hydrocarbons, in preference to their saturated analogs. These and other objects will become apparent hereinafter.

DETAILED DESCRIPTION OF THE INVENTION

The invention resides in an improved Fischer-Tropsch process for the selective preparation of low molecular weight olefinic hydrocarbons from carbon monoxide/hydrogen mixtures, the improvement consisting in the use of a perovskite catalyst having the empirical formula $AB_{1-a}Fe_aO_3$ wherein:

A is at least one of Na, K, Rb, Cs, Fr, Be, Mg, Ca, Sr, Ba, Ra, La, Ce, Pr, Nd, Pm, Sm, Eu, Gd, Tb, Dy, Ho, Er, Tm, Yb, Lu, Th or U;

B is at least one of Al, Ga, In, Tl, Ge, Sn, Pb, Sc, Y, Ti, Zr, Hf, V, Nb, Ta, Cr, Mo, W, Mn, Tc, Re, Ru, Os, Co, Rh, Ir, Ni, Pd, Pt, Cu, Ag, Au, Zn, Cd or Hg; and a is within the range 0.01 to 1.

In the aforesaid formula, A and B are chosen in concert in accordance with known oxidation state and ionic radius rules as required to produce the perovskite [$ABO_3$] crystal structure and allowing for deviation from the ideal stoichiometry of oxygen by ±0.5, that is, $O_{2.5-3.5}$.

In the aforesaid formula, for preferred catalysts of the invention, a is within the range 0.1 to 1; A is Ba, La or Sr; and B is Mn, Ti or Zr.

By "low molecular weight hydrocarbon" is meant a $C_{2-6}$ hydrocarbon. By "selective preparation of low molecular weight olefinic hydrocarbons" is meant that the $C_{2-6}$ hydrocarbons which are prepared by means of this invention comprise a major olefinic hydrocarbon fraction and a minor saturated hydrocarbon fraction.

The carbon monoxide/hydrogen mixtures, for example, synthesis gas, which are employed as the starting material in the process of this invention, are converted to the desired olefinic hydrocarbons by passing the mixture, as a gas, through a reactor, for example, glass, containing a catalytic amount of the catalyst at a temperature of 200° C. to 400° C., preferably 300° C. to 380° C. Preferably, but optionally, the catalyst is prereduced in the presence of hydrogen at an elevated temperature for an extended period of time, for example, at 400° C. for 18 hours, before being contacted with the carbon monoxide/hydrogen mixture. The carbon monoxide/hydrogen pressure should be in the range 1 psia to 2000 psia (6.894 kPa to 13.788 MPa), preferably 15 psia to 1000 psia (103.410 kPa to 6.894 MPa). The molar ratio of hydrogen/carbon monoxide fed to the reactor should be in the range 0.3 to 1.5. The preferred ratio is 0.6 to 0.7. The space velocity of the carbon monoxide/hydrogen gas mixture to the reactor should be in the range 1 to 100 minutes$^{-1}$. The preferred range is 5 to 10 minutes$^{-1}$.

The catalysts which are useful in this invention can be prepared from oxide mixtures or from mixtures of nitrate, hydroxide or carbonate precursors of the oxides. The oxide mixture is heated at 900° C. for 100 hours to produce the desired $AB_{1-a}Fe_aO_3$ perovskite structure.

CATALYST PREPARATION

The preparation of catalysts used in the examples which were carried out to demonstrate the invention are described in the experiments which follow. In both the experiments and the examples provided hereinbelow temperatures are in degrees Celsius.

EXPERIMENT 1

Preparation of LaFeO$_3$

La(NO$_3$)$_3$·6H$_2$O (65.0 g) and Fe(NO$_3$)$_3$·9H$_2$O (48.4 g) were dissolved in 1000 mL of water. The water was removed from this solution by heating under vacuum. The crude solid was dried in the vacuum oven and dired at 900° for 4 days. After each 24 h the sample was removed from the oven, cooled, ground and thoroughly mixed.

EXPERIMENT 2

Preparation of LaMn$_{0.5}$Fe$_{0.5}$O$_3$

One hundred mL of a 1M aqueous solution of La(NO$_3$)$_3$ was combined with 50 mL of a 1M aqueous solution of Fe(NO$_3$)$_3$. Mn(OOCCOO)·2H$_2$O (8.95 g) was dissolved in the combined solution. The water was removed from the solution by heating under vacuum. The crude solid was dried in a vacuum oven at 95° and fired at 900° for 4 days. After each 24 h the sample was removed from the oven, cooled, ground and thoroughly mixed.

EXPERIMENT 3

Preparation of $SrTi_{0.9}Fe_{0.1}O_3$

One hundred mL of a 1M aqueous solution of $Sr(NO_3)_2$ was combined with 10 mL of a 1M aqueous solution of $Fe(NO_3)_3$. Titanium dioxide (7.19 g) was suspended in the combined solution. The water was removed from the solution by heating under vacuum. The crude solid was dried in a vacuum oven and fired at 900° for 100 h. After each 24 h the sample was removed from the oven, cooled, ground and thoroughly mixed.

EXPERIMENT 4

Preparation of $BaTi_{0.9}Fe_{0.1}O_3$

One hundred mL of a 1M aqueous solution of $Ba(NO_3)_2$ was combined with 10 mL of a 1M aqueous solution of $Fe(NO_3)_3$. Titanium dioxide (7.19 g) was suspended in the combined solution. The water was removed from the solution by heating under vacuum. The crude solid was dried in a vacuum oven and fired at 900° for 100 h. After each 24 h the sample was removed from the oven, cooled, ground and thoroughly mixed.

EXPERIMENT 5

Preparation of $LaZr_{0.5}Fe_{0.5}O_3$

One hundred mL of a 1M aqueous solution of $La(NO_3)_3$ was combined with 50 mL of a 1M aqueous solution of $Fe(NO_3)_3$. Zirconium dioxide (61.61 g) was suspended in the combined solution. The water was removed from the solution by heating under vacuum. The crude solid was dried in a vacuum oven and fired at 900° for 100 hr. After each 24 h the sample was removed from the oven, cooled, ground and thoroughly mixed.

EXPERIMENT 6

Preparation of $SrZr_{0.9}Fe_{0.1}O_3$

One hundred mL of a 1M aqueous solution of $Sr(NO_3)_2$ was combined with 10 mL of a 1M aqueous solution of $Fe(NO_3)_3$. Zirconium dioxide (110.9 g) was suspended in the combined solution. The water was removed from the solution by heating under vacuum. The crude solid was dried in a vacuum oven and fired at 900° for 100 h. After each 24 h the sample was removed from the oven, cooled, ground and thoroughly mixed.

All of the above catalysts were examined by X-ray diffraction to verify the perovskite structure.

Catalyst Testing

The general procedure used to carry out the process of the invention in the examples provided hereinbelow, using the catalysts prepared in Experiments 1 to 6, is as follows. Powdered catalyst (2 mL) was placed in a U-tube inside a safety barricade which contained a fluidized sand bath heater. CO and $H_2$ were metered and mixed before entering the reaction zone.

Catalysts were tested within the range 300° to 380°. Usually, one hour was required to obtain and stabilize the temperature when changing from one temperature to another.

Product Analysis

A two-column, three-detector system was required to analyze the wide roduct spectrum. A Porapak TM Q+5A Molecular Sieve+Ucon TM 1800 first column separated materials from $H_2$ and hydrocarbons having up to five carbon atoms, and a second Ucon TM 50 column was used to analyze for hydrocarbons having more than five carbon atoms. With two sample loops, a Valco valving system, a hot wire and flame ionization on the second column, both types of product could be analyzed simultaneously.

Throughout the examples the percentage figures are mole percentages.

EXAMPLE 1

Reaction of $CO/H_2$ with $LaFeO_3$

The catalyst (from Experiment 1) was prereduced at 400° for 18 h in the presence of hydrogen. The $H_2/CO$ ratio was 0.67 and the GHSV (Gas Hourly Space Velocity) was 500 $h^{-1}$. A GHSV of 500 $h^{-1}$ corresponds to a space velocity of $8\frac{1}{3}$ minutes$^{-1}$, that is, within the preferred range of 5 to 10 minutes$^{-1}$. The results are listed in Table 1.

TABLE 1

| Temperature | 300° | 340° | 380° |
|---|---|---|---|
| CO Conversion | 6.5% | 7.7% | 3.0% |
| CO to $CO_2$ | 36.9% | 41.2% | 59.0% |
| CO to Hydrocarbons | 63.1% | 58.8% | 41.0% |
| % Species in Product | | | |
| Methane | 3.7% | 5.7% | 26.8% |
| Ethylene | 5.8% | 7.8% | 6.8% |
| Ethane | 0.5% | 0.8% | 0.4% |
| Propylene | 6.2% | 7.9% | 6.3% |
| Propane | 0.3% | 0.5% | 0.7% |
| Butenes | 2.8% | 3.3% | 2.9% |
| Butane + Butadiene | 1.7% | 1.6% | 2.5% |
| $C_5$ Hydrocarbons | 5.4% | 4.6% | 17.2% |
| $C_6$ Hydrocarbons | 39.2% | 60.1% | 28.4% |
| $C_7$ Hydrocarbons | 18.6% | 5.6% | 4.1% |
| $C_8$ Hydrocarbons | 15.9% | 2.2% | 4.5% |
| $C_9$ and Higher Hydrocarbons | 0% | 0% | 0% |
| Methanol | 0% | 0% | 0% |
| Dimethyl Ether | 0% | 0% | 0% |
| Ethanol | 0% | 0% | 0% |

EXAMPLE 2

Reaction of $CO/H_2$ with $LaZr_{0.5}Fe_{0.5}O_3$

The catalyst (from Experiment 5) was prereduced at 400° for 18 h in the presence of hydrogen. The $H_2/CO$ ratio was 0.67 and the GHSV was 500 $h^{-1}$. The results are listed in Table 2.

TABLE 2

| Temperature | 300° | 340° | 380° |
|---|---|---|---|
| CO Conversion | 0.24% | 0.32% | 1.61% |
| CO to $CO_2$ | 51% | 50% | 55% |
| CO to Hydrocarbons | 49% | 50% | 45% |
| % Species in Product | | | |
| Methane | 4.2% | 8.3% | 12.6% |
| Ethylene | 7.3% | 13.0% | 20.5% |
| Ethane | 0.4% | 0.6% | 1.0% |
| Propylene | 31.0% | 29.6% | 25.4% |
| Propane | 0% | 5.8% | 3.0% |
| Butenes | 6.6% | 5.6% | 6.2% |
| Butane + Butadiene | 0% | 1.0% | 0.8% |
| $C_5$ Hydrocarbons | 51.3% | 17.5% | 8.9% |
| $C_6$ Hydrocarbons | 0% | 3.5% | 5.4% |
| $C_7$ Hydrocarbons | 0% | 20.9% | 17.5% |
| $C_8$ Hydrocarbons | 0% | 0% | 1.8% |
| $C_9$ and Higher | 0% | 0% | 0% |

TABLE 2-continued

| Hydrocarbons | | | |
|---|---|---|---|
| Methanol | 0% | 0% | 0% |
| Dimethyl Ether | 0% | 0% | 0% |
| Ethanol | 0% | 0% | 0% |

EXAMPLE 3

Reaction of $CO/H_2$ with $LaMn_{0.5}Fe_{0.5}O_3$

The catalyst (from Experiment 2) was prereduced at 400° for 18 h in the presence of hydrogen. The $H_2/CO$ ratio was 0.67 and the GHSV was 500 $h^{-1}$. The results are listed in Table 3.

TABLE 3

| Temperature | 300° | 340° | 380° |
|---|---|---|---|
| CO Conversion | 0.71% | 1.1% | 3.2% |
| CO to $CO_2$ | 65.7% | 57.4% | 69.3% |
| CO to Hydrocarbons | 34.3% | 42.6% | 30.7% |
| % Species in Product | | | |
| Methane | 15.0% | 12.1% | 25.1% |
| Ethylene | 14.9% | 14.2% | 21.9% |
| Ethane | 5.2% | 3.7% | 2.1% |
| Propylene | 20.6% | 17.8% | 18.5% |
| Propane | 2.7% | 1.6% | 1.0% |
| Butenes | 4.1% | 3.9% | 5.7% |
| Butane + Butadiene | 6.9% | 5.1% | 1.7% |
| $C_5$ Hydrocarbons | 10.9% | 8.2% | 6.0% |
| $C_6$ Hydrocarbons | 19.5% | 30.4% | 9.4% |
| $C_7$ Hydrocarbons | 0% | 0.8% | 3.3% |
| $C_8$ Hydrocarbons | 0% | 2.2% | 6.6% |
| $C_9$ and Higher Hydrocarbons | 0% | 0% | 0% |
| Methanol | 0% | 0% | 0% |
| Dimethyl Ether | 0% | 0% | 0% |
| Ethanol | 0% | 0% | 0% |

EXAMPLE 4

Reaction of $CO/H_2$ with $SrTi_{0.9}Fe_{0.1}O_3$

The catalyst (from Experiment 3) was prereduced at 400° for 18 h in the presence of hydrogen. The $H_2/CO$ ratio was 0.67 and the GHSV was 500 $h^{-1}$. The results are listed in Table 4.

TABLE 4

| Temperature | 300° | 340° | 380° |
|---|---|---|---|
| CO Conversion | 0.2% | 0.51% | 1.0% |
| CO to $CO_2$ | 93.0% | 86.6% | 81.9% |
| CO to Hydrocarbons | 7.0% | 13.4% | 18.1% |
| % Species in Product | | | |
| Methane | 55.0% | 29.2% | 29.1% |
| Ethylene | 12.1% | 18.8% | 24.6% |
| Ethane | 0% | 2.2% | 2.1% |
| Propylene | 14.1% | 23.5% | 20.1% |
| Propane | 0% | 1.9% | 1.5% |
| Butenes | 0% | 12.9% | 8.2% |
| Butane + Butadiene | 0% | 0% | 0.7% |
| $C_5$ Hydrocarbons | 0% | 11.5% | 4.0% |
| $C_6$ Hydrocarbons | 0% | 0% | 0% |
| $C_7$ Hydrocarbons | 0% | 0% | 4.8% |
| $C_8$ Hydrocarbons | 0% | 0% | 0% |
| $C_9$ and Higher Hydrocarbons | 0% | 0% | 5.8% |
| Methanol | 9.4% | 0% | 0% |
| Dimethyl Ether | 9.4% | 0% | 0% |
| Ethanol | 0% | 0% | 0% |

EXAMPLE 5

Reaction of $CO/H_2$ with $BaTi_{0.9}Fe_{0.1}O_3$

The catalyst (from Experiment 4) was prereduced at 400° for 18 h in the presence of hydrogen. The $H_2/CO$ ratio was 0.67 and the GHSV was 500 $h^{-1}$. The results are listed in Table 5.

TABLE 5

| Temperature | 300° | 340° | 380° |
|---|---|---|---|
| CO Conversion | 0.3% | 0.4% | 0.5% |
| CO to $CO_2$ | 83.1% | 83.0% | 85.8% |
| CO to Hydrocarbons | 16.9% | 17.0% | 14.2% |
| % Species in Product | | | |
| Methane | 11.3% | 14.2% | 25.9% |
| Ethylene | 8.6% | 9.2% | 11.5% |
| Ethane | 0.5% | 2.8% | 1.2% |
| Propylene | 39.2% | 37.8% | 32.3% |
| Propane | 0% | 10.2% | 7.5% |
| Butenes | 11.7% | 16.6% | 13.6% |
| Butane + Butadiene | 0.8% | 0% | 0% |
| $C_5$ Hydrocarbons | 18.0% | 9.2% | 8.1% |
| $C_6$ Hydrocarbons | 0% | 0% | 0% |
| $C_7$ Hydrocarbons | 0% | 0% | 0% |
| $C_8$ Hydrocarbons | 0% | 0% | 0% |
| $C_9$ and Higher Hydrocarbons | 0% | 0% | 0% |
| Methanol | 0% | 0% | 0% |
| Dimethyl Ether | 0% | 0% | 0% |
| Ethanol | 0% | 0% | 0% |

EXAMPLE 6

Reaction of $CO/H_2$ with $SrZr_{0.9}Fe_{0.1}O_3$

The catalyst (from Experiment 6) was prereduced at 400° for 18 h in the presence of hydrogen. The $H_2/CO$ ratio was 0.67 and the GHSV was 500 $h^{-1}$. The results are listed in Table 6.

TABLE 6

| Temperature | 380° |
|---|---|
| CO Conversion | 0.15% |
| CO to $CO_2$ | 87.5% |
| CO to Hydrocarbons | 12.5% |
| % Species in Product | |
| Methane | 14.5% |
| Ethylene | 10.1% |
| Ethane | 1.1% |
| Propylene | 65.4% |
| Propane | 0% |
| Butenes | 8.9% |
| Butane + Butadiene | 0% |
| $C_5$ Hydrocarbons | 0% |
| $C_6$ Hydrocarbons | 0% |
| $C_7$ Hydrocarbons | 0% |
| $C_8$ Hydrocarbons | 0% |
| $C_9$ and Higher Hydrocarbons | 0% |
| Methanol | 0% |
| Dimethyl Ether | 0% |
| Ethanol | 0% |

The above detailed description of the invention, including the embodiments exemplified, and the claims recited hereinbelow will render obvious to one skilled in the art numerous additional embodiments within the scope of the invention. All such additional embodiments are intended to be within the scope of the invention as claimed hereinbelow.

I claim:

1. In a process for the selective, catalytic gas phase preparation of low molecular weight olefins from mixtures of $H_2$ and CO, the improvement consisting of contacting and reacting a mixture of $H_2$ and CO, at a $H_2/CO$ molar ratio within the range 0.3 to 1.5, at a space velocity of 1 to 100 minutes$^{-1}$, at a pressure of 1 to 2000 psia (6.894 kPa to 13.788 MPa), at a temperature within the range 200° to 400° C., in the presence of the catalyst of the empirical formula $AB_{1-a}Fe_aO_3$ wherein:

A is at least one of Na, K, Rb, Cs, Fr, Be, Mg, Ca, Sr, Ba, Ra, La, Ce, Pr, Nd, Pm, Sm, Eu, Gd, Tb, Dy, Ho, Er, Tm, Yb, Lu, Th or U;

B is at least one of Al, Ga, In, Tl, Ge, Sn, Pb, Sc, Y, Ti, Zr, Hf, V, Nb, Ta, Cr, Mo, W, Mn, Tc, Re, Ru, Os, Co, Rh, Ir, Ni, Pd, Pt, Cu, Ag, Au, Zn, Cd or Hg; and a is within the range 0.01 to 1, provided, however, in the aforesaid formula, A and B are chosen in concert in accordance with known oxidation state and ionic radius rules as required to produce the perovskite ($ABO_3$) crystal structure and allowing for deviation from the ideal stoichiometry of oxygen by ±0.5.

2. Process of claim 1 wherein the $H_2/CO$ molar ratio is within the range 0.6 to 0.7, the space velocity is 5 to 10 minutes$^{-1}$, the pressure is 15 to 1000 psia (103.410 kPa to 6.894 MPa), and the temperature is within the range 300° to 380° C.

3. Process of claim 1 wherein the catalyst is prereduced at an elevated temperature in the presence of $H_2$ before being contacted with the mixture of $H_2$ and CO.

4. Process of claim 3 wherein the catalyst is prereduced at 400° C. for eighteen hours.

5. Process of claim 1 wherein the catalyst is $LaFeO_3$.

6. Process of claim 1 wherein the catalyst is $LaZr_{0.5}Fe_{0.5}O_3$.

7. Process of claim 1 wherein the catalyst is $LaMn_{0.5}Fe_{0.5}O_3$.

8. Process of claim 1 wherein the catalyst is $SrTi_{0.9}Fe_{0.1}O_3$.

9. Process of claim 1 wherein the catalyst is $BaTi_{0.9}Fe_{0.1}O_3$.

10. Process of claim 1 wherein the catalyst is $SrZr_{0.9}Fe_{0.1}O_3$.

11. Process of claim 1 wherein, in the formula, a is within the raange 0.1 to 1, A is Ba, La or Sr, and B is Mn, Ti or Zr.

* * * * *